US 10,568,548 B2

(12) United States Patent
Menzel

(10) Patent No.: US 10,568,548 B2
(45) Date of Patent: Feb. 25, 2020

(54) DEVICE, SYSTEM, AND METHOD FOR PATIENT FALL DETECTION

(71) Applicant: Mindray DS USA, Inc., Mahwah, NJ (US)

(72) Inventor: Frank Menzel, Oakland, NJ (US)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 957 days.

(21) Appl. No.: 14/476,560

(22) Filed: Sep. 3, 2014

(65) Prior Publication Data
US 2016/0058330 A1 Mar. 3, 2016

(51) Int. Cl.
*A61B 5/11* (2006.01)
*A61B 5/00* (2006.01)

(52) U.S. Cl.
CPC .......... *A61B 5/1117* (2013.01); *A61B 5/747* (2013.01)

(58) Field of Classification Search
None
See application file for complete search history.

(56) References Cited

U.S. PATENT DOCUMENTS

| 7,974,689 | B2* | 7/2011 | Volpe | A61B 5/0404 607/6 |
| 9,615,777 | B2* | 4/2017 | Cloutier | A61B 5/0002 |
| 2010/0121226 | A1* | 5/2010 | Ten Kate | A61B 5/1117 600/595 |
| 2011/0201972 | A1* | 8/2011 | Ten Kate | G08B 21/0446 600/595 |
| 2013/0054180 | A1* | 2/2013 | Barfield | G01P 15/0891 702/138 |
| 2015/0123785 | A1* | 5/2015 | Haflinger | A61B 5/6831 340/539.11 |
| 2015/0269826 | A1* | 9/2015 | Zhang | G08B 21/0446 340/539.12 |

* cited by examiner

*Primary Examiner* — Sean P Dougherty
*Assistant Examiner* — Benjamin S Melhus
(74) *Attorney, Agent, or Firm* — Kory D. Christensen

(57) ABSTRACT

A portable telemetry device includes a physiological component, a fall detector component, a radio, and a communication component. The physiological component is configured to receive, from at least one sensor, physiological data representative of a physiological condition of a patient. The fall detector component is configured to detect a fall of the portable telemetry device. The radio is configured to wirelessly send radio signals. The communication component is configured to transmit the physiological data and an indication of the fall to a monitoring system using the radio.

13 Claims, 3 Drawing Sheets

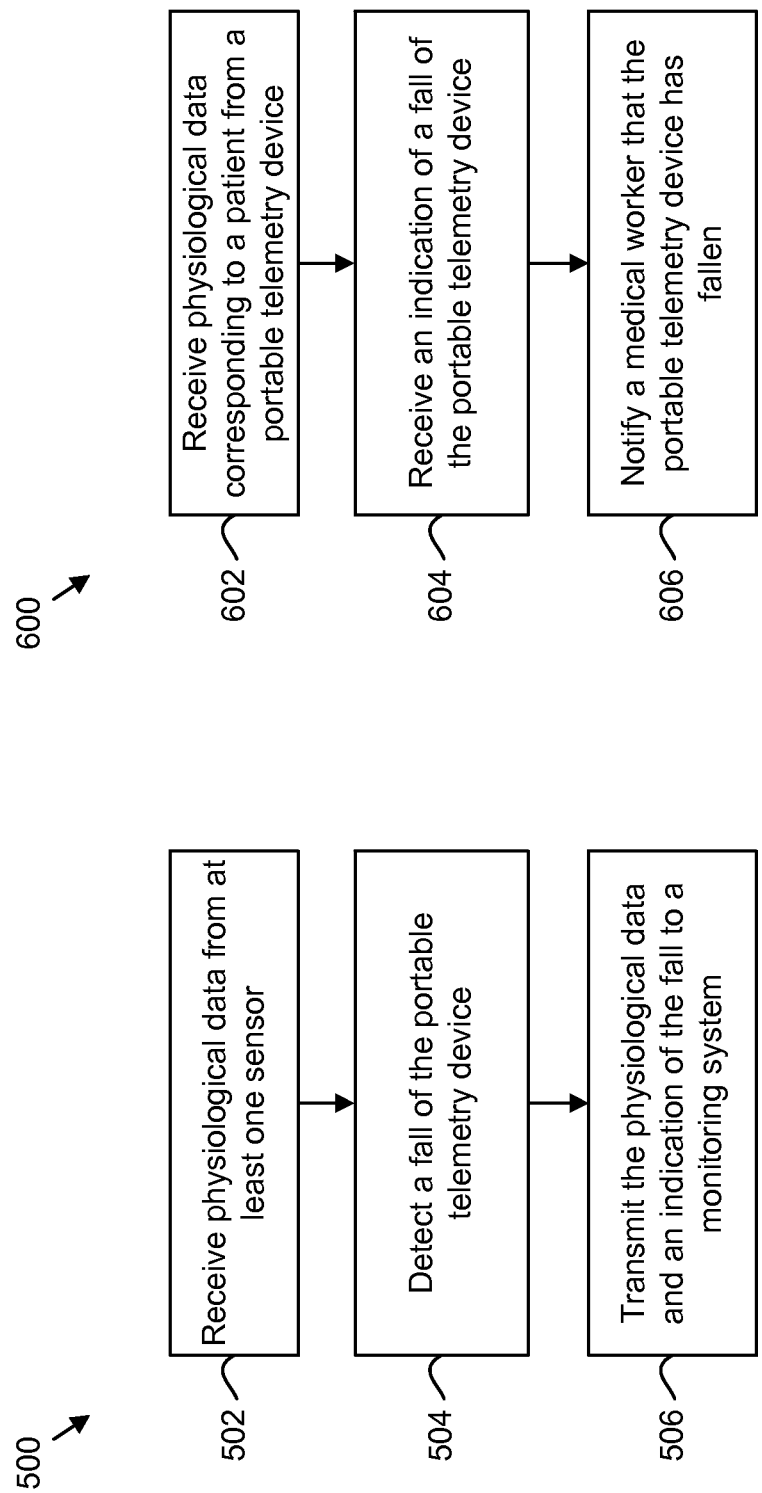

DEVICE, SYSTEM, AND METHOD FOR PATIENT FALL DETECTION

TECHNICAL FIELD

The present disclosure relates to medical monitoring and more particularly relates to systems, methods, and devices for detecting a fall of a patient.

BRIEF DESCRIPTION OF THE DRAWINGS

FIG. 5 is a schematic flow chart diagram illustrating a method for detecting a fall of a patient, according to one embodiment.

FIG. 6 is a schematic flow chart diagram illustrating another method for detecting a fall of a patient, according to one embodiment.

DETAILED DESCRIPTION OF PREFERRED EMBODIMENTS

Modern medical practice makes extensive use of electronic monitoring of vital signs and other physiological parameters of patients. In some cases, remote monitoring of physiological parameters, or telemetry, is used to allow nurses, doctors, and/or computing devices to determine the health of a patient or detect problems with the patient when the nurse, doctor, or other medical worker is not physically present with the patient. In some cases, wireless telemetry devices worn by a patient may allow the patient to move around and/or be easily moved between locations while maintaining monitoring of the patient's vital signs. One example of a portable telemetry device is the Mindray Telepack®.

In some situations, due to age, illness, surgery, medications, or the like, patients may be weak or otherwise negatively affected and unable to perform some physical tasks to their full ability. For example, these patients may be at risk for falling when standing, walking, or getting out of bed. If patients are not monitored closely, they can fall and suffer injuries without knowledge of medical staff. Generally, the more quickly medical staff can detect a fall, the better the patient outcome, as any injuries or discomfort can be addressed quickly.

In light of the foregoing, Applicants disclose devices, systems, and methods for detecting a fall of a patient. In one embodiment, a portable telemetry device includes a physiological component, a fall detector component, a radio, and a communication component. The physiological component is configured to receive, from at least one sensor, physiological data representative of a physiological condition of a patient. The fall detector component is configured to detect a fall of the portable telemetry device. In one embodiment, the portable telemetry device is configured to attach to the patient. The radio is configured to wirelessly send radio signals. The communication component is configured to transmit the physiological data and an indication of the fall to a monitoring system using the radio. In some embodiments, the portable telemetry device is configured to detect a connection status of one or more sensors to determine whether the patient has fallen.

Figure 1:
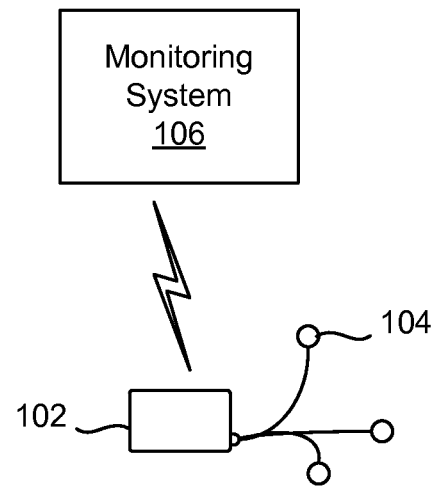
FIG. 1 is a schematic block diagram illustrating a telemetry system, according to one embodiment.

Turning to the figures, FIG. 1 is a schematic diagram illustrating a monitoring system 106 and a portable telemetry device 102 for medical telemetry. In one embodiment, the portable telemetry device 102 includes a telemetry device worn by a patient. For example, the patient may be free to walk or move while wearing the portable telemetry device 102 due to size, weight, and/or capability for wireless communication.

The portable telemetry device 102 may include a portable device comprising a housing containing a processor, circuitry, computer readable memory, an antenna, radios, a battery, an accelerometer, and/or the like. The portable telemetry device 102 may have a size such that it can be worn by a patient while allowing the patient to move freely. The portable telemetry device 102 may include one or more ports for coupling to sensors and receiving signals from the sensors. The portable telemetry device 102 may include a human-machine interface, which may include a display, one or more buttons, and/or indicator lights to allow a human to determine a status of the portable telemetry device 102, enter information, or otherwise interact with the portable telemetry device 102.

The portable telemetry device 102 is in wireless communication with the monitoring system 106. Connected to the portable telemetry device 102 are a plurality of sensors 104 which may be used to measure patient parameters and/or obtain patient waveforms. For example, the sensors 104 may include one or more electrocardiography (ECG) sensors, a pulse oximetry sensor (e.g., $SpO_2$), and/or any other sensors. The portable telemetry device 102 may receive signals from the sensors 104 as analog or digital data signals indicating a physiological condition of a patient.

The portable telemetry device 102 may also obtain movement data from a movement sensor connected to the portable telemetry device 102 or integrated within the housing of the portable telemetry device 102. In one embodiment, the portable telemetry device 102 may detect a fall of the portable telemetry device 102 or patient based on the movement data. The portable telemetry device 102 may correlate connection or disconnection of the sensors with a fall to determine whether a patient has fallen or just the portable telemetry device 102. In one embodiment, the portable telemetry device 102 may send physiological parameters and information about a fall to the monitoring system 106. For example, the portable telemetry device 102 may forward processed or unprocessed sensor data, fall data, or other data to the monitoring system 106 so that a doctor, a nurse, and/or other medical personnel can monitor a condition of the patient.

The monitoring system 106 may include a computing device such as a computer, a server, or the like. The monitoring system 106 may include a processor, circuitry, computer readable memory, an antenna, radios, communication ports, and/or the like. In one embodiment, the monitoring system 106 includes a computing system. For example, the monitoring system 106 may include a computing system for a nursing station, an intensive care ward, a step down ward, and/or an in-patient ward.

The monitoring system 106 receives the physiological data and information about a fall from the portable telemetry device 102 and stores and/or processes the data. In one embodiment, the monitoring system 106 stores the physiological data and fall data in memory for later access and/or analysis. In one embodiment, the monitoring system 106 processes the physiological data and/or movement data to detect problems in relation to the patient, detect whether there is an alarm condition, determine whether a patient has fallen, or perform other analysis. For example, the monitoring system 106 may report an alarm condition or fall to a nurse, a doctor, or other medical personnel.

The monitoring system 106 may also provide control data to the portable telemetry device 102 to configure alarm settings, reset alarms, determine a state or location of the portable telemetry device 102, transfer stored data, or otherwise configure operation of the portable telemetry device 102. In one embodiment, the monitoring system 106 may send control data to the portable telemetry device 102 and receive control data from the portable telemetry device 102 to determine that messages were received or that instructions corresponding to control data were performed.

Figure 2:
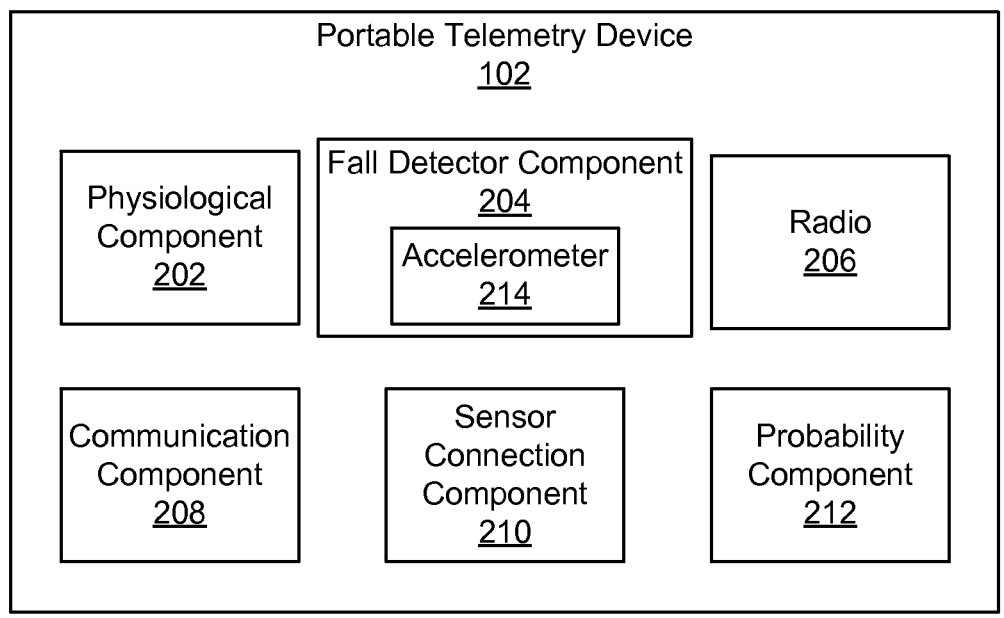
FIG. 2 is a schematic block diagram illustrating a portable telemetry device, according to one embodiment.

FIG. 2 is a schematic block diagram illustrating components of a portable telemetry device 102, according to one embodiment. The portable telemetry device 102 includes a physiological component 202, a fall detector component 204, a radio 206, a communication component 208, a sensor connection component 210, and a probability component 212. The components 202-212 are given by way of example only and may not all be included in all embodiments. In some embodiments, one or more of the components 202-212 may be located in a remote monitoring system 106. For example, the monitoring system 106 may include the probability component 212 and may process any information about a fall or physiological data received from the portable telemetry device 102.

The physiological component 202 is configured to receive physiological data of a patient. The physiological data may be based on signals or data received from one or more sensors 104 in communication with the portable telemetry device 102. For example, the physiological component 202 may receive signals or data from the one or more sensors 104 of FIG. 1 that are connected to the portable telemetry device 102. The physiological data may include ECG data, $SpO_2$ data, or any other type of data representative of a physiological condition of the patient.

The fall detector component 204 is configured to detect a fall of the portable telemetry device 102 or patient. In one embodiment, the fall detector component 204 may include an accelerometer 214, such as a three-axis accelerometer. The accelerometer 214 may be mounted within a housing of the portable telemetry device 102. The accelerometer 214 may produce one or more electrical signals to indicate movements, rotations, and/or accelerations of the portable telemetry device 102. In one embodiment, the fall detector component 204 may detect movement of the patient by detecting movement of the portable telemetry device 102. For example, the portable telemetry device 102 may be connected or attached to a patient so that when the patient moves, the portable telemetry device 102 moves with the patient.

In one embodiment, the fall detector component 204 may process one or more outputs from an accelerometer 214 to identify what a patient is doing. Different movements have different signatures which can be detected. In one embodiment, the sensor connection component 210 may detect an activity movement including information about a current static position of a patient. For example, if a three-axis accelerometer is used, an orientation of the portable telemetry device 102 can be determined and a corresponding position of the patient may be detected. In one embodiment, the fall detector component 204 detects a waveform signature from an accelerometer 214 corresponding to the patient falling down, standing up, sitting down, walking, or the like.

In one embodiment, the fall detector component 204 may detect a fall by detecting that the portable telemetry device 102 is in free fall based on output from the accelerometer 214. The fall detector component 204 may also detect other events in relation to a fall, such as the beginning of free fall, or that the portable telemetry device 102 appears to be accelerating or moving in a manner that indicates that the portable telemetry device 102 is about to fall. The fall detector component 204 may also detect one or more impacts associated with a fall, such as reaching the end of a sensor lead, impacting a table or bed, and/or impacting a floor.

The radio 206 may include a radio that is configured to communicate wirelessly using radio signals. The radio 206 may be configured to operate according to a wireless standard. Example wireless standards include an institute for electrical and electronics engineers (IEEE) 802.11 standard (known to industry groups as Wi-Fi), a cellular communication standard (such as 3GPP LTE), a Bluetooth standard, or another standard. Similarly, the radio 206 may be configured to operate within a licensed or unlicensed band. One example of licensed bands in the United States is the wireless medical telemetry service (WMTS) bands, which include dedicated protected bands that have been allocated for medical telemetry purposes. One example of unlicensed bands is the widely used industrial, scientific, and medical (ISM) radio bands. The frequency band and standard may vary considerably and may allow the portable telemetry device 102 to communicate with a monitoring system 106.

The communication component 208 is configured to communicate data with the monitoring system 106. For example, the communication component 208 may transmit the physiological data and an indication that a fall has been detected (or other movement data) to a monitoring system 106 using the radio 206. In one embodiment, the communication component 208 transmits physiological data or movement data (such as an indication of a fall) that has been generated by the physiological component 202 or fall detector component 204. For example, signals from a sensor 104 or an accelerometer 214 may be converted to a digital format or other format that can be understood and processed by the monitoring system 106. In one embodiment, some data may be transmitted in a raw format (e.g., analog or sampled format) to be processed by the monitoring system 106.

The communication component 208 may also communicate other types of data such as a fall alarm or control data. In one embodiment, the communication component 208 may receive control data to configure operation of the portable telemetry device 102. For example, the control data may indicate that certain types of parameters are to be gathered and sent or that certain types of parameters are no longer needed. In one embodiment, the communication component 208 may receive information that indicates a threshold level for an alarm or a type of event or movement activity that should trigger an alarm. In one embodiment, the communication component 208 may transmit an indication that an alarm condition has been detected.

A sensor connection component 210 is configured to determine a status of a sensor connection of one or more sensors 104. In one embodiment, the sensor connection component 210 may determine whether patient data is being received from a specific sensor 104. For example, a sensor connection may include a connection to a patient (e.g., the sensor 104 is connected to a patient) and a connection to the portable telemetry device 102 (e.g., via a sensor lead). If the sensor 104 is not connected to the patient or the portable telemetry device 102, the sensor connection component 210 may determine that the specific sensor 104 has a disconnected status. In other words, patient data is not being received at the portable telemetry device 102 for the specific sensor 104. Alternatively, if the sensor 104 is connected to both the patient and the portable telemetry device 102, the sensor connection component 210 may determine that the specific sensor 104 has a connected status. In other words, patient data is being received at the portable telemetry device 102 for the specific sensor 104. The sensor connection component 210 may detect when a connection between a sensor lead (e.g., an electrical, pneumatic, or other connection) and a port of the portable telemetry device 102 is lost. For example, a switch, button, capacitor, or other device may detect when a sensor lead is plugged into a port.

In one embodiment, the sensor connection component 210 may provide information about the connection status to the fall detector component 204. The fall detector component 204 may determine whether a patient has fallen based on the connection status. In one embodiment, if the fall detector component 204 detects a fall of the portable telemetry device 102, the fall detector component 204 is configured to determine that the patient has also fallen in response to the sensor connection component 210 determining that the sensor 104 has a connected status. For example, if the portable telemetry device 102 has fallen and is still connected to a patient, it may be more likely that the patient has also fallen. In one embodiment, if the fall detector component 204 detects a fall of the portable telemetry device 102, the fall detector component 204 is configured to determine that the patient has not fallen in response to the sensor connection component 210 determining that the sensor 104 has a disconnected status. For example, if the portable telemetry device 102 has fallen and is not connected to a patient, it may be more likely that the patient has not fallen.

In one embodiment, the sensor connection component 210 may detect a change in status for a sensor 104. For example, the sensor connection component 210 may detect a specific time at which one or more sensors 104 had a connected status and changed to a disconnected status. In one embodiment, the sensor connection component 210 or fall detector component 204 may determine a relative timing of the change in connection status corresponding to the fall. For example, the sensor connection component 210 and/or fall detector component 204 may determine that one or more sensors 104 were disconnected before a fall, during free fall, or following an impact.

Figure 4:
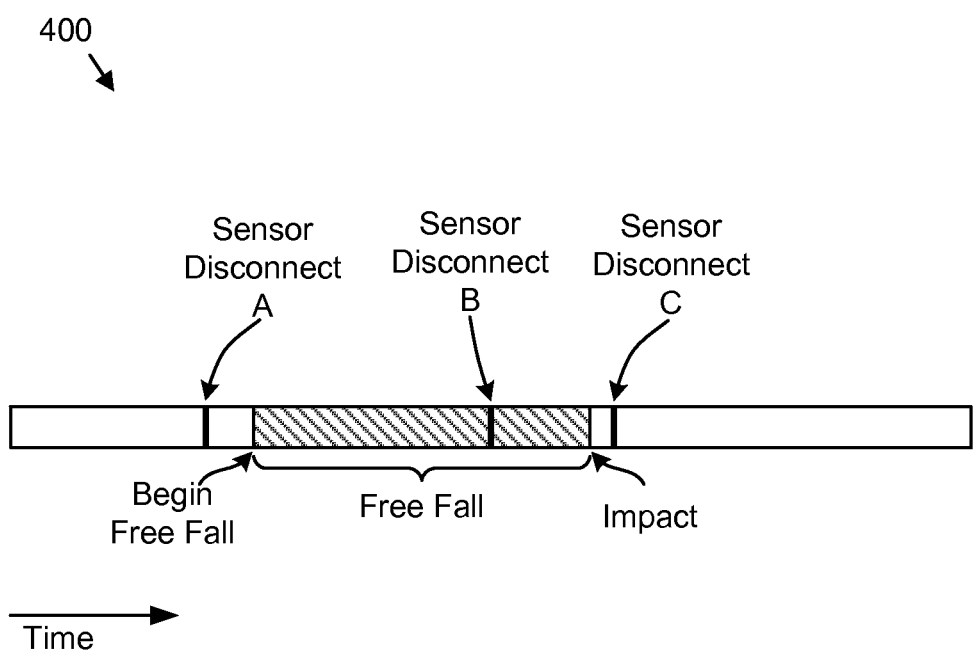
FIG. 4 is a schematic diagram illustrating a timing of a sensor disconnect in relation to a fall of a portable telemetry device, according to one embodiment.

FIG. 4 is a schematic diagram 400 illustrating example timing of disconnection of one or more sensors 104 in relation to events of a free fall. Specifically, a time period is illustrated where the portable telemetry device 102, as determined by the fall detector component 204, begins free fall, is in free fall, and impacts an object, such as the ground. Three different disconnection events are illustrated: sensor disconnect A, which occurs before the beginning of free fall; sensor disconnect B, which occurs during free fall (e.g., after the beginning of free fall but before impact, such as impact with the floor); and sensor disconnect C, which occurs after free fall (e.g., after impact). In one embodiment, the sensor connection component 210 detects a timing of a change in sensor connection status, which may allow the fall detector component 204 to determine whether a patient has fallen or whether only the portable telemetry device 102 has fallen.

Returning to FIG. 2, a probability component 212 is configured to determine a probability level that a patient has fallen. In one embodiment, the probability component 212 determines the probability level based on the movement data from the fall detector component 204 and/or a connection status determined by the sensor connection component 210. In one embodiment, the probability component 212 determines that it is more likely that a patient has fallen when the sensor connection component 210 determines that one or more sensors 104 had a connected status in relation to a fall detected by the fall detector component 204. In one embodiment, the probability component 212 determines that it is less likely that a patient has fallen when the sensor connection component 210 determines that one or more sensors 104 had a disconnected status in relation to a fall detected by the fall detector component 204.

In one embodiment, the probability component 212 determines a probability level that the patient fell based on the timing of the disconnected status. For example, if the disconnected status occurred before the portable telemetry device 102 began free fall (see sensor disconnect A of FIG. 4), then the probability component 212 may determine that there is a reduced level of probability that the patient fell. As another example, if the disconnected status occurred during free fall (after the beginning of free fall and before a final impact; see sensor disconnect B of FIG. 4), then the probability component 212 may determine that there is a medium level of probability that the patient fell. As yet another example, if the disconnected status occurred after a final impact (see sensor disconnect C of FIG. 4) or a connected status continues even after the fall, then the probability component 212 may determine that there is a high level of probability that the patient fell.

In one embodiment, the probability component 212 may provide the probability level to a communication component 208 for communication to a monitoring system 106. For example, the monitoring system 106 may determine whether or not to issue an alarm based on the probability level or may provide the probability level to a medical worker as part of an alarm or notification.

Figure 3:
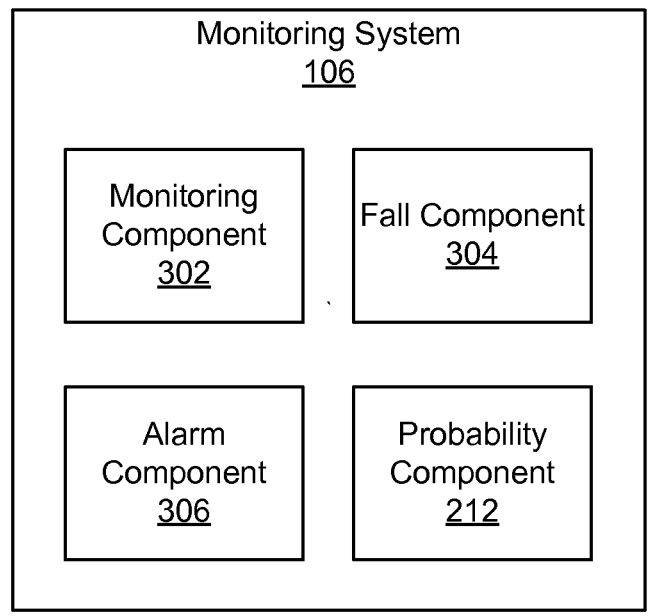
FIG. 3 is a schematic block diagram illustrating components of a monitoring system, according to one embodiment.

FIG. 3 is a schematic block diagram illustrating components included in a monitoring system 106, according to one embodiment. The monitoring system 106 includes a monitoring component 302, a fall component 304, and an alarm component 306. The monitoring system 106 may also include a probability component 212. The components 302-306 and 212 are given by way of example only and may not all be included in all embodiments.

The monitoring component 302 is configured to receive data from the portable telemetry device 102. The monitoring component 302 may also store or evaluate the data. In one embodiment, the monitoring component 302 processes physiological parameters to detect alarm conditions or a health status of one or more patients with one or more corresponding portable telemetry devices 102. For example, a nurse or other medical worker may be able to remotely monitor the patient's physiological status by viewing sensor data for the patient. The monitoring component 302 may also receive movement data for processing or storage, or may provide the movement data to the fall component 304 and/or alarm component 306. In one embodiment, the monitoring component 302 receives information regarding a sensor connection and/or a timing of a sensor disconnection.

The fall component 304 is configured to determine that a portable telemetry device 102 has fallen. In one embodiment, the fall component 304 determines that a remote telemetry device 102 has fallen based on an indication of a fall received from the portable telemetry device 102. For example, the fall component 304 may receive an indication that the portable telemetry device 102 has fallen from the communication component 208 in response to the fall detector component 204 detecting the fall. The fall component 304 may also receive a sensor connection status. In one embodiment, the fall component 304 may determine whether a patient has fallen based on a sensor connection status.

An alarm component 306 is configured to provide an alarm in response to an alarm condition. In one embodiment, the alarm component 306 provides an alarm in response to a physiological condition of the patient, as determined from physiological data from the one or more sensors 104. For example, an alarm condition may be set up to trigger an alarm in response to detection of a physiological condition. In one embodiment, the alarm component 306 is configured to notify a medical worker that the portable telemetry device 102 has fallen. Thus, medical personnel can quickly go assist the patient. The alarm component 306 may provide any other information regarding the fall to the medical worker. For example, the notification may include an indication that a patient has fallen, a probability level that the patient has fallen, a sensor connection status, or the like. The alarm component 306 may provide the notification by displaying a message on a display screen, such as a display screen in communication with the monitoring system 106. In one embodiment, the alarm component 306 sends a paging message to a medical worker who is responsible for the patient. For example, the paging message may be sent to a mobile phone, portable patient monitor, or the like to allow a nurse or medical worker who may not be present with the monitoring system 106 that the patient or portable telemetry device 102 has fallen.

The probability component 212 of the monitoring system 106 may be configured to perform any of the same functionality discussed above in relation to the probability component 212 of the portable telemetry device 102. For example, the probability component 212 may determine a probability level that the patient fell based on the status of the sensor connection and provide the probability level to the alarm component 306 to report to the medical worker. In one embodiment, the probability component 212 may determine a probability level that the patient has fallen, in response to receiving an indication of a sensor connection status and a timing of the status in relation to the fall.

FIG. 5 is a schematic flow chart diagram illustrating a method 500 for detecting a fall of a patient, according to one embodiment. In one embodiment, the method 500 is performed by a portable telemetry device 102, such as the portable telemetry device 102 of FIG. 2.

The method 500 begins and a physiological component 202 receives 502 physiological data representative of a physiological condition of a patient. For example, the portable telemetry device 102 may be connected to one or more sensors 104, such as ECG or $SpO_2$ sensors, to monitor a physiological condition of the patient. The physiological component 202 may receive 502 the physiological data in digital or analog format from the sensors 104.

A fall detector component 204 detects 504 a fall of the portable telemetry device 102. In one embodiment, the portable telemetry device 102 is configured to attach to a patient such that movements of the portable telemetry device 102 may correspond to movements of the patient. The fall detector component 204 may detect 504 the fall based on movement data, such as sensor data or a waveform from an accelerometer 214 or other sensor that can detect physical movement. In one embodiment, the portable telemetry device 102 is attached to the patient such that the portable telemetry device 102 rotates, tilts, and moves with the patient.

A communication component 208 transmits 506 the physiological data and an indication of the fall to a monitoring system 106 using a radio 206. For example, the monitoring system 106 may monitor the physiological parameters and the reported data to allow a nurse or other medical worker to detect a fall of the patient as well as monitor a physiological condition. Thus, a medical worker may be able to determine that a patient appears to be in an acceptable physiological state but has fallen down. In one embodiment, a probability level that the patient fell, a sensor connection status, or other information may also be transmitted 506 to the monitoring system 106.

FIG. 6 is a schematic flow chart diagram illustrating a method 600 for detecting a fall of a patient, according to one embodiment. The method 600 may be performed by a monitoring system 106, such as the monitoring system 106 of FIG. 3.

The method 600 begins and a monitoring component 302 receives 602 physiological data representative of a physiological condition. For example, the monitoring component 302 may receive 602 the physiological data from one or more portable telemetry devices 102 which are used to monitor one or more corresponding patients. The patient data may include any type of physiological or patient data discussed herein.

A fall component 304 receives 604 an indication that a fall occurred from the portable telemetry device 102. For example, the fall component 304 may receive 604 an indication that the portable telemetry device 102 has fallen. The fall component 304 may also receive other information regarding the fall, such as a probability level that the patient has fallen, or an indication regarding a connection status of one or more sensors 104 in relation to the fall.

An alarm component 306 notifies 606 a medical worker that the portable telemetry device 102 has fallen. The alarm component 306 may notify 606 the medical worker by displaying a pop-up message or other indication on a display screen, playing a sound, vibrating a portable electronic device, or the like. In one embodiment, the alarm component 306 notifies 606 the medical worker by sending the notification to a portable patient monitor corresponding to the medical worker. The medical worker can go to assist the patient, if needed, in response to the notification.

Various techniques, or certain aspects or portions thereof, may take the form of program code (i.e., instructions) embodied in tangible media, such as floppy diskettes, CD-ROMs, hard drives, a non-transitory computer readable storage medium, or any other machine readable storage medium, wherein when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, an EPROM, a flash drive, an optical drive, a magnetic hard drive, or another medium for storing electronic data. One or more programs that may implement or utilize the various techniques described herein may use an application programming interface (API), reusable controls, and the like. Such programs may be implemented in a high-level procedural or an object-oriented programming language to communicate with a computer system. However, the program(s) may be implemented in assembly or machine language, if desired. In any case, the language may be a compiled or an interpreted language, and combined with hardware implementations.

It should be understood that many of the functional units described in this specification may be implemented as one or more components, which is a term used to more particularly emphasize their implementation independence. For example, a component may be implemented as a hardware circuit comprising custom very large scale integration (VLSI) circuits or gate arrays, off-the-shelf semiconductors such as logic chips, transistors, or other discrete components. A component may also be implemented in programmable hardware devices such as field programmable gate arrays, programmable array logic, programmable logic devices, or the like.

Components may also be implemented in software for execution by various types of processors. An identified component of executable code may, for instance, comprise one or more physical or logical blocks of computer instructions, which may, for instance, be organized as an object, a procedure, or a function. Nevertheless, the executables of an identified component need not be physically located together, but may comprise disparate instructions stored in different locations that, when joined logically together, comprise the component and achieve the stated purpose for the component.

Indeed, a component of executable code may be a single instruction, or many instructions, and may even be distributed over several different code segments, among different programs, and across several memory devices. Similarly, operational data may be identified and illustrated herein within components, and may be embodied in any suitable form and organized within any suitable type of data structure. The operational data may be collected as a single data set, or may be distributed over different locations including over different storage devices, and may exist, at least partially, merely as electronic signals on a system or network. The components may be passive or active, including agents operable to perform desired functions.

Reference throughout this specification to an "example" means that a particular feature, structure, or characteristic described in connection with the example is included in at least one embodiment of the present invention. Thus, appearances of the term "example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on its presentation in a common group without indications to the contrary. In addition, various embodiments and examples of the present invention may be referred to herein along with alternatives for the various components thereof. It is understood that such embodiments, examples, and alternatives are not to be construed as de facto equivalents of one another, but are to be considered as separate and autonomous representations of the present invention.

It will be obvious to those having skill in the art that many changes may be made to the details of the above-described embodiments without departing from the underlying principles of the invention. The scope of the present invention should, therefore, be determined only by the following claims.

The invention claimed is:

1. A patient-worn portable telemetry device in wireless communication with a remote monitoring system comprising a display screen, the portable telemetry device for providing physiological data and fall detection for a patient, comprising:

at least one physiological sensor connected to a patient that monitors one or more vital signs of the patient and generates physiological data, wherein a representation of the physiological data is displayed on the display screen of the remote monitoring system;

an accelerometer that generates movement data indicative of physical movement of the portable telemetry device including whether the portable telemetry device is in freefall;

a processor that determines a likelihood of whether the patient has fallen based on a timing of the portable telemetry device being in freefall relative to a timing of a change in connection status of the at least one physiological sensor, wherein the connection status is determined at least in part based on whether data is not being received from the at least one physiological sensor, wherein the processor determines the likelihood the patient has fallen is higher if the at least one physiological sensor becomes disconnected while the portable telemetry device is in freefall than if the at least one physiological sensor becomes disconnected before the portable telemetry device is in freefall; and a radio that wirelessly transmits to the remote monitoring system an indication of the likelihood of whether the patient has fallen, wherein the indication triggers an alarm on the remote monitoring system.

2. The portable telemetry device of claim 1, wherein the processor determines the connection status at least in part in response to whether a lead from the at least one physiological sensor is plugged into at least one port of the portable telemetry device.

3. The portable telemetry device of claim 1, wherein the processor determines the likelihood of whether the patient has fallen based at least in part on a waveform signature of a motion detected by the accelerometer.

4. The portable telemetry device of claim 3, wherein the waveform signature is consistent with the portable telemetry device being in freefall.

5. The portable telemetry device of claim 3, wherein the waveform signature is consistent with the portable telemetry device impacting an object.

6. The portable telemetry device of claim 1, wherein the processor further determines the likelihood the patient has fallen is higher if the at least one physiological sensor becomes disconnected a period of time after an impact as determined by the movement data than if the at least one physiological sensor becomes disconnected while the portable telemetry device is in freefall.

7. The portable telemetry device of claim 1, wherein the processor determines the likelihood of whether the patient has fallen based on a timing of a change in connection status relative to movement data provided by the accelerometer.

8. The portable telemetry device of claim 7, wherein the processor determines that it is unlikely the patient has fallen when the connection status indicates that the at least one physiological sensor becomes disconnected before the portable telemetry device is in free fall as determined by the accelerometer.

9. The portable telemetry device of claim 7, wherein the processor determines it is likely that the patient has fallen when the connection status indicates that the at least one physiological sensor becomes disconnected after the portable telemetry device impacts an object as determined by the accelerometer.

10. The portable telemetry device of claim 1, wherein the remote monitoring system stores in a memory device the fall data and the physiological data so that the processor can later determine the likelihood of a fall.

11. A patient-worn portable telemetry device in wireless communication with a remote monitoring system for providing physiological data and fall detection for a patient, the remote monitoring system comprising a display screen, the portable telemetry device comprising:
- at least one physiological sensor connected to a patient that monitors one or more vital signs of the patient and generates physiological data for display on the display screen of the remote monitoring system;
- an accelerometer that generates movement data indicative of physical movement of the portable telemetry device including whether the portable telemetry device is in freefall;
- a processor that determines a likelihood of whether the patient has fallen based on a timing of the at least one physiological sensor becoming disconnected from the portable telemetry device relative to a timing of the portable telemetry device being in freefall; wherein the processor determines that the likelihood is higher if the at least one physiological sensor becomes disconnected during freefall than if the at least one physiological sensor becomes disconnected before freefall; and wherein the processor determines that the at least one physiological sensor is disconnected based at least in part on data no longer being received by the portable telemetry device from the at least one physiological sensor; and
- a radio that wirelessly transmits to the monitoring system an indication of the likelihood of whether the patient has fallen, wherein the indication triggers an alarm on the remote monitoring system.

12. The portable telemetry device of claim 11, wherein the processor determines that the likelihood is higher if the at least one physiological sensor becomes disconnected or remains connected after freefall than if the at least one physiological sensor becomes disconnected before or during freefall.

13. The portable telemetry device of claim 11, wherein the processor determines that the at least one physiological sensor is disconnected based at least in part on a loss of an electrical connection between the least one physiological sensor and the portable telemetry device.

* * * * *